United States Patent
Lee et al.

(10) Patent No.: US 8,700,889 B2
(45) Date of Patent: Apr. 15, 2014

(54) SYSTEM AND METHOD OF SHARING WEB PAGE THAT REPRESENTS HEALTH INFORMATION

(75) Inventors: Kwang-hyeon Lee, Seoul (KR); Kyu-tae Yoo, Seongnam-si (KR)

(73) Assignee: Samsung Electronics Co., Ltd. (KR)

( * ) Notice: Subject to any disclaimer, the term of this patent is extended or adjusted under 35 U.S.C. 154(b) by 785 days.

(21) Appl. No.: 12/757,189

(22) Filed: Apr. 9, 2010

(65) Prior Publication Data

US 2011/0010534 A1    Jan. 13, 2011

(30) Foreign Application Priority Data

Jul. 7, 2009    (KR) .................. 10-2009-0061723

(51) Int. Cl.
*H04L 29/06* (2006.01)
*H04L 9/32* (2006.01)
*G06F 7/04* (2006.01)
*G06F 15/16* (2006.01)
*G06F 17/30* (2006.01)

(52) U.S. Cl.
USPC .................. 713/150; 726/3; 726/26; 713/176

(58) Field of Classification Search
USPC ........................ 726/26, 3; 713/176
See application file for complete search history.

(56) References Cited

U.S. PATENT DOCUMENTS

| | | | |
|---|---|---|---|
| 6,956,698 B2 | 10/2005 | Li et al. | |
| 7,523,505 B2* | 4/2009 | Menschik et al. | 726/26 |
| 7,543,149 B2* | 6/2009 | Ricciardi et al. | 713/176 |
| 7,801,422 B2* | 9/2010 | Wright et al. | 369/47.12 |
| 8,458,202 B2* | 6/2013 | Noumeir | 707/756 |
| 2002/0038388 A1* | 3/2002 | Netter | 709/318 |
| 2006/0177114 A1* | 8/2006 | Tongdee et al. | 382/128 |
| 2006/0273356 A1 | 12/2006 | Matsumoto et al. | |
| 2008/0016155 A1 | 1/2008 | Khalatian | |
| 2008/0243539 A1* | 10/2008 | Barish et al. | 705/2 |
| 2009/0007237 A1* | 1/2009 | Lorsch | 726/3 |
| 2009/0313304 A1* | 12/2009 | Goodger et al. | 707/104.1 |

FOREIGN PATENT DOCUMENTS

| | | |
|---|---|---|
| JP | 2004-102863 A | 4/2004 |
| JP | 2006-148063 A | 6/2006 |
| KR | 1020010049547 A | 6/2001 |
| KR | 100593835 B1 | 6/2006 |
| KR | 1020080026917 A | 3/2008 |
| KR | 1020090001565 A | 1/2009 |

\* cited by examiner

*Primary Examiner* — Shin-Hon Chen
(74) *Attorney, Agent, or Firm* — Cantor Colburn LLP

(57) ABSTRACT

A method of displaying health information of a user, the method including: monitoring if a sharing request for a health information of a user is made by an external device, which provides a web page representing the health information of the user in the form of an image; downloading a captured image of the web page from the external device if the sharing request for the health information of the user is made; and displaying the downloaded captured image.

20 Claims, 7 Drawing Sheets

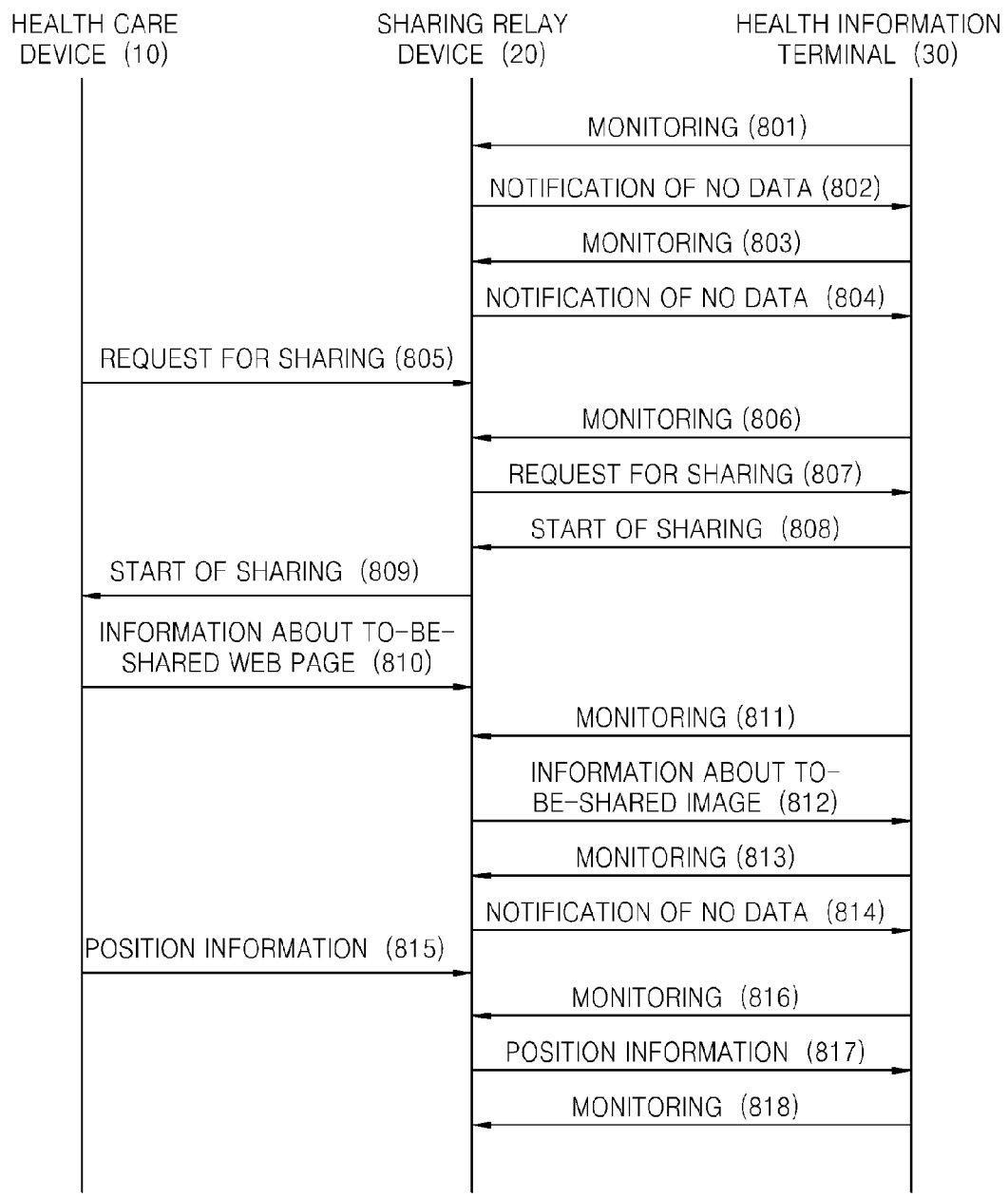

SYSTEM AND METHOD OF SHARING WEB PAGE THAT REPRESENTS HEALTH INFORMATION

CROSS-REFERENCE TO RELATED APPLICATIONS

This application claims priority to Korean Patent Application No. 10-2009-0061723, filed on Jul. 7, 2009, and all the benefits accruing therefrom under U.S.C. §119, the content of which in its entirety is herein incorporated by reference.

BACKGROUND

1. Field

The present disclosure relates to a system and a method of sharing a web page that represents health information.

2. Description of the Related Art

At present, research is being actively conducted to establish a remote medical system, which provides medical information and medical services to remote locations, and provides a remote health monitoring service. In a remote medical service, health information of a patient is shared between a health care service provider and the patient. With widespread access to the Internet, a service which allows a patient to consult with a health care service provider without visiting the hospital and allows the hospital to ascertain the health status of the patient is being widely used. To use this service, health information terminals which transmit and receive the health information of patients are being used in the home. However, even when an electronic medical record ("EMR") is used, it is not easy for patients to share their medical record, if they do not visit a health care service provider.

SUMMARY

Provided is a method and a system which allows a health care device of a health care service provider and a health information terminal of a user to share some a component of a web page which represent health information of a user and which is expressed as an image, in real time. Also provided is a computer-readable recording medium having recorded thereon a computer program for executing the method. Additional aspects will be set forth in part in the description which follows and, in part, will be apparent from the description.

According to an aspect, a method of displaying health information of a user includes monitoring whether a sharing request for a health information of a user is made by an external device, wherein the external device provides a web page representing the health information of the user in the form of an image; downloading a captured image of the web page from the external device when the sharing request for the health information of the user is made; and displaying the downloaded captured image.

Also disclosed is a method of providing health information of a user in the form of an image, the method includes transforming a web page, which represents the health information of the user, into an image; storing the image; and transmitting the stored image to a terminal of the user in response to a download request of the terminal of the user.

Also disclosed is a computer-readable recording medium having recorded thereon a computer program for executing a method of displaying health information of a user, the method comprising: monitoring whether a sharing request for a health information of a user is made by an external device, wherein the external device provides a web page representing the health information of the user in the form of an image; downloading a captured image of the web page from the external device when the sharing request for the health information of the user is made; and displaying the downloaded captured image.

Also disclosed is a computer-readable recording medium having recorded thereon a computer program for executing the method of providing the health information of the user.

Also disclosed is an apparatus for displaying health information of a user, the apparatus including: a monitoring unit, which monitors if a sharing request for a health information of a user is made by an external device, which provides a web page representing the health information of the user in the form of an image; a communications interface, which downloads a captured image of the web page from the external device, if the monitoring unit determines that the sharing request for the health information of the user is made; and a display unit, which displays the downloaded captured image.

Also disclosed is an apparatus for providing health information of a user in the form of an image, the apparatus including a transformation unit, which transforms a web page, which represents a health information of a user, into an image; a database, which stores the image; and a communications interface, which transmits the stored image to a terminal of the user in response to a download request by the user's terminal.

Also disclosed is a system for sharing a web page which represents health information of a user, the system including a health care device, which transmits a sharing request for a web page representing a health information of a user to a sharing relay device; wherein the sharing relay device transforms a to-be-shared portion of the web page received from the health care device into an image, stores the image, and transmits the stored image to a terminal of the user in response to a download request of the user's terminal; and a health information terminal, which monitors the sharing relay device to determine if a sharing request for the health information of the user is made by the health care device, wherein if the health information terminal determines that the sharing request for the health information of the user is made, downloading the stored image from the sharing relay device and displaying the downloaded image.

BRIEF DESCRIPTION OF THE DRAWINGS

These and/or other aspects will become apparent and more readily appreciated from the following detailed description, taken in conjunction with the accompanying drawings in which:

FIG. 8 is an exemplary embodiment of a data flow diagram illustrating when a health care device, the sharing relay device, and the health information terminal included in the health information image sharing system illustrated in FIG. 1 share a health information image.

DETAILED DESCRIPTION

Figure 1:
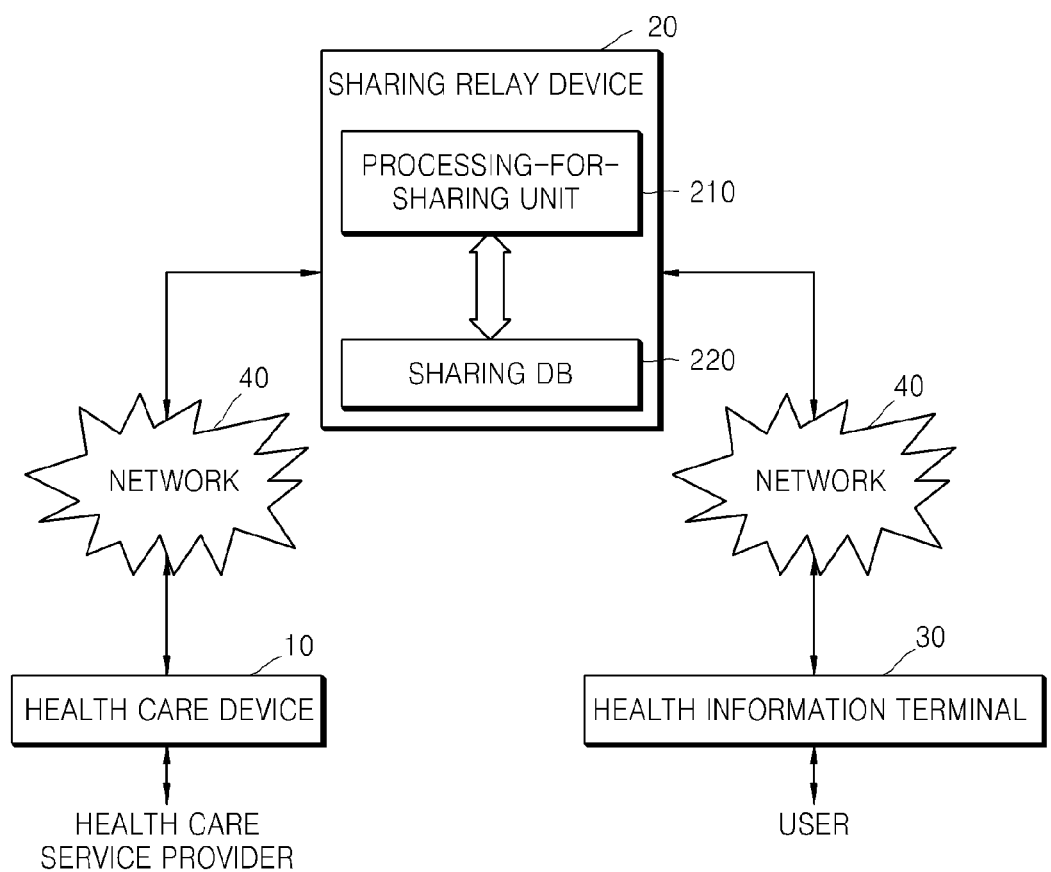
FIG. 1 is a block diagram illustrating an exemplary embodiment of a structure of a health information image sharing system.

Reference will now be made in detail to embodiments, examples of which are illustrated in the accompanying drawings, wherein like reference numerals refer to like elements throughout. In this regard, the present embodiments may have different forms and should not be construed as being limited to the descriptions set forth herein. Accordingly, the embodiments are merely described below, by referring to the figures, to explain aspects of the present disclosure.

It will be understood that when an element is referred to as being "on" another element, it can be directly on the other element or intervening elements may be present therebetween. In contrast, when an element is referred to as being "directly on" another element, there are no intervening elements present. As used herein, the term "and/or" includes any and all combinations of one or more of the associated listed items.

It will be understood that, although the terms first, second, third etc. may be used herein to describe various elements, components, regions, layers and/or sections, these elements, components, regions, layers and/or sections should not be limited by these terms. These terms are only used to distinguish one element, component, region, layer or section from another element, component, region, layer or section. Thus, a first element, component, region, layer or section discussed below could be termed a second element, component, region, layer or section without departing from the teachings of the present invention.

The terminology used herein is for the purpose of describing particular embodiments only and is not intended to be limiting. As used herein, the singular forms "a," "an" and "the" are intended to include the plural forms as well, unless the context clearly indicates otherwise. It will be further understood that the terms "comprises" and/or "comprising," or "includes" and/or "including" when used in this specification, specify the presence of stated features, regions, integers, steps, operations, elements, and/or components, but do not preclude the presence or addition of one or more other features, regions, integers, steps, operations, elements, components, and/or groups thereof.

Furthermore, relative terms, such as "lower" or "bottom" and "upper" or "top," may be used herein to describe one element's relationship to another elements as illustrated in the Figures. It will be understood that relative terms are intended to encompass different orientations of the device in addition to the orientation depicted in the Figures. For example, if the device in one of the figures is turned over, elements described as being on the "lower" side of other elements would then be oriented on "upper" sides of the other elements. The exemplary term "lower," can therefore, encompasses both an orientation of "lower" and "upper," depending on the particular orientation of the figure. Similarly, if the device in one of the figures is turned over, elements described as "below" or "beneath" other elements would then be oriented "above" the other elements. The exemplary terms "below" or "beneath" can, therefore, encompass both an orientation of above and below.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and the present disclosure, and will not be interpreted in an idealized or overly formal sense unless expressly so defined herein.

FIG. 1 is a block diagram illustrating an exemplary embodiment of a structure of a health information image sharing system. Referring to FIG. 1, the health information image sharing system includes a health care device 10, a sharing relay device 20, and a health information terminal 30. The sharing relay device 20 includes a processing-for-sharing unit 210 and a sharing database ("DB") 220. The health care device 10 may be controlled by a health care service provider, the health information terminal 30 may be controlled by a user, and data is transmitted and received between the health care device 10 and the sharing relay device 20 or between the health information terminal 30 and the sharing relay device 20 via a network 40. In an embodiment, the network 40 may comprise a plurality of networks, specifically a first network and a second network.

The health care device 10 communicates with the sharing relay device 20 in order to share a web page, which represents health information of a user, with the health information terminal 30. The web page is displayed in the form of an image. The health care service provider, which may control the health care device 10, may be a health care professional, but is not limited thereto. Examples of the health care professional include a doctor, a nurse, or the like. The health care service provider may manipulate the health care device 10 so that the health care device 10 and the health information terminal 30 share an image, which represents the health information of the user. Although it will be hereinafter explained for clarity and convenience of explanation that the health care service provider controls the health care device 10 in order to share the image, which represents the health information of the user, embodiments are not limited thereto. In another embodiment, a user may control a health information terminal, for example. The health care service provider may control the health care device 10 by using a general-use computer, a personal digital assistant ("PDA"), or the like, in order to share the image, which represents the health information of the user, with the health information terminal 30.

The sharing relay device 20 provides the health information of the user in the form of an image to the health information terminal 30. In an embodiment, image sharing between the health care device 10 and the health information terminal 30 is achieved via the sharing relay device 20. The sharing relay device 20 transmits and receives data to and from at least one of the health care device 10 and the health information terminal 30, captures a portion or an entirety of a web page, transforms the captured web page into an image, stores the image, performs encryption on the transmitted and received data according to a usage setting, and transforms position information about a portion of the image into normalized standard position information.

The health information terminal 30 displays the user's health information, which is shared with the health care device 10. In an embodiment, the health information terminal 30 communicates with the sharing relay device 20 in order to share, with the health care device 10, a web page in the form of an image, which represents the health information of the user. The health information terminal 30 allows health-related information to be transmitted and received between a user and a health care professional, such as a health care professional who cares for the health of the user. A user who controls the health information terminal 30 may be a patient, and a user of the health information terminal 30, who desires to care for the health of the user, or another user, may be included as a user who controls the health information terminal 30. The health information terminal 30 may be an independent device or may be in combination with a general-use computer, a PDA, or the like, or a combination thereof. Because the health information terminal 30 shares an image with the health care device 10 via the sharing relay device 20 by operating in connection with the health care device 10, an independent application, which is different from a web application, may be driven in the health information terminal 30.

The network 40 is a communication medium disposed between the health care device 10 and the sharing relay device 20, or disposed between the health information terminal 30 and the sharing relay device 20. The network 40 may comprise an Internet, a Local Area Network ("LAN"), a wireless LAN, a Wide Area Network ("WAN"), or the like, or a combination thereof. In an embodiment, the network may be another type of network, which is capable of transmitting and receiving information.

Connection and data communication between the health care device 10 and the sharing relay device 20 may be performed using a server/client connection method. If the network 40 is the Internet, for example, data may be transmitted and received across the internet between a server and a client, by using a Transmission Control Protocol/Internet Protocol ("TCP/IP"), for example. An Internet service may include an information search service, and a web browser may be an application program, which provides data search and data exchange between Internet hosts. Pieces of information of an Internet host may be constructed in a hypertext format, and the pieces of information in the hypertext format may be transmitted and received using a HyperText Transfer Protocol ("HTTP"). The pieces of information constructed in the hypertext format may be provided from a web server to a client, and in turn the client may output the pieces of information in the form of a web page by using a web application. The information pieces constructed in the hypertext format may be written in a HyperText Markup Language ("HTML"), which is a language in which hyper texts are expressed. HTML is an example of a language, which may be used to create a web page. Exemplary languages also include an eXtensible Hypertext Markup Language ("XHTML"), a Cascading Style Sheet ("CSS"), a Java script, or the like, which may be used to construct a web page.

When a client inputs a Uniform Resource Locator ("URL") in order to access a web server in which search information has been stored, the web browser of the client analyzes the URL, accesses a server indicated by the URL according to a result of the analysis, and sends a request to the server to transmit data. In response to the request, the server provides data, which constitutes a web page, to the client. The client displays the received data in the form of a web page by using the web browser, for example, which is an example of a web application. In an exemplary server/client system, a connection between a server and a client is established at the request of the client. After the server and the client are connected to each other, the client requests data transmission, using an HTTP request, for example, and the server transmits data in response to the request. The server/client system is known to one of ordinary skill in the art, and thus a detailed description thereof will be omitted.

The HTTP is a protocol which may provide communication between a server and a client in a web environment. Documents having a hypertext format on the web may be accessed using the HTTP. The HTTP is connectionless and stateless. As used herein, the term "stateless" denotes non-maintenance of a state. When it is said that the HTTP does not maintain a state, although a server and a client are connected to each other, the server does not store the state of the client, and thus the state of the client is not maintained and a command is independently handled during every execution of a request. For example, in an embodiment wherein the client requests data transmission via his or her web browser, the server does not store the request of the client in order to transmit and receive data to and from a plurality of clients, thereby conserving the server's resources. Accordingly, when the server and the client perform consecutive operations, previous information is not maintained, and thus services such as data trace, user recognition, and the like may not be provided.

The health care service provider allows the health information of the user to be displayed in the form of a web page on the health care device 10. As further described above, if the health care service provider shares the web page representing the health information of the user with the user, by using a general-use computer, a portable digital terminal, or the like, or a combination thereof, the health care service provider may allow the web page to be displayed on the general-use computer, the portable digital terminal, or the like, or a combination thereof, by requesting data from the health care device 10 by using the general-use computer, the portable digital terminal, or the like, or a combination thereof.

Since the health care device 10 includes a web application, the web page which represents the health information of the user may be displayed on the health care device 10. Alternatively, the health care service provider may be connected to the health care device 10 by selecting the URL of the health care device 10 through the general-use computer, the portable digital terminal, or the like, or a combination thereof, of the health care service provider, and the general-use computer, the portable digital terminal, or the like, or a combination thereof of the health care service provider may transmit an HTTP request to the health care device 10 in order to request data transmission, and may receive the requested data from the health care device 10. The received data is displayed in the form of a web page on the general-use computer, the portable digital terminal, or the like, or a combination thereof of the health care service provider, and thus the health care service provider may refer to the user's health information, which is displayed in the form of a web page.

In an embodiment, the health care device 10 may be used as both a server and a client. The health care device 10 may serve as a server because it stores the health information of the user, or may serve as a client because it may receive information from the health information terminal 30 or display a web page by using a web browser.

The health care device 10 and the sharing relay device 20 may communicate with each other using the TCP/IP, which is a standard protocol of the Internet. When a server and a client are connected to each other by the server/client system, the client may not be able to receive data from the server in real time. When the client and the server are disconnected from each other, a connection port between the client and the server may be closed, and thus states associated with the connection may be lost because the HTTP is connectionless and stateless.

Accordingly, the sharing DB 220 of the sharing relay device 20 may store images to be shared, and the health information terminal 30 may receive the to-be-shared images from the sharing DB 220. Since the health information terminal 30 may request the sharing relay device 20 to transmit data frequently, real-time sharing between the health care device 10 and the health information terminal 30 may be improved or substantially ensured. In addition, when data is transmitted and received between the health information terminal 30 and the health care device 10, although the connection between the health information terminal 30 and the health care device 10 may be concluded (e.g., closed), information about the health information terminal 30 may be continuously stored in the sharing relay device 20.

Since the health information terminal 30 may transmit and receive the health information of the user to and from the health care device 10, an independent application different from a web application may be installed in the health information terminal 30.

Although the sharing relay device 20 and the health care device 10 may be separate devices, they may be incorporated (e.g., integrated) into a single unitary body. For example, a function of the sharing relay device 20 may be included in the health care device 10.

Figure 2:
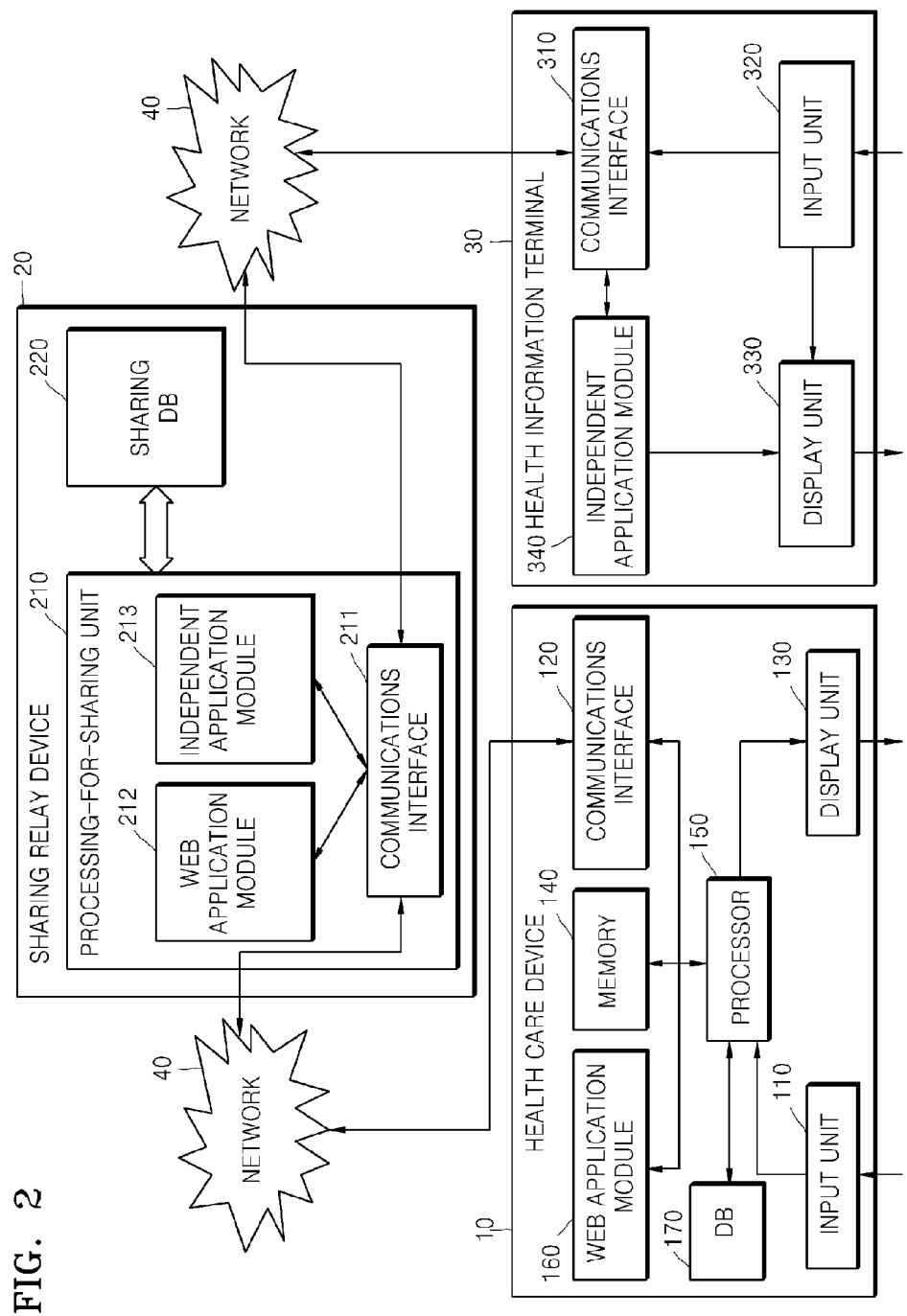
FIG. 2 is a block diagram illustrating the structure of the health information image sharing system illustrated in FIG. 1, in further detail.

FIG. 2 is a block diagram illustrating the structure of the health information image sharing system illustrated in FIG. 1, in further detail. Referring to FIG. 2, the health care device 10 includes a first input unit 110, a first communications interface 120, a first display unit 130, a memory 140, a processor 150, a web application module 160, and a database ("DB") 170. The sharing relay device 20 includes the processing-for-sharing unit 210 and the sharing DB 220. The processing-for-sharing unit 210 includes a second communications interface 211, a web application module 212, and a first independent application module 213. The health information terminal 30 includes a third communications interface 310, a second input unit 320, a second display unit 330, and a second independent application module 340. In this disclosure, only components which are related to a system of sharing a web page, which represents health information, will be described to provide a full, simple and clear explanation of the system. In addition, it will be understood by one of ordinary skill in the art that other general-use components may be included in addition to the components illustrated in FIG. 2.

The health care device 10 communicates with the sharing relay device 20 in order to share the web page representing the user's health information with the health information terminal 30, and receives an input signal corresponding to a user's input from the sharing relay device 20. Referring to FIG. 2, as described above, the health care device 10 includes the first input unit 110, the first communications interface 120, the first display unit 130, the memory 140, the processor 150, the web application module 160, and the DB 170.

The first input unit 110 may be used by the health care service provider to input a signal. For example, by manipulating the first input unit 110, the health care service provider may input a signal for displaying the user's health information on the first display unit 130, may input a request indicating a desire to share images with the health information terminal 30, may input a signal for generating an image which represents the user's health information which is desired to be shared with the health information terminal 30, and selects an emphasized location or a marked location by selecting, clicking, or dragging the first input unit 110. The first input unit 110 may include any device which used to input the signal from the health care service provider. For example, the first input unit 110 may include a keyboard, a mouse, a touch pad, an audio recognition device, or the like, or a combination thereof.

The health information of the user is information about any value, health-check result, graph, state, or symptom which may be related to the health of the user. For example, the health information of the user may be brain wave analysis data, an electromyogram, a body temperature, a blood pressure, a body weight, an obesity index, a body fat mass, a liver value, a cholesterol value, a blood sugar value, or the like, or a combination thereof. The health information of the user may include various documents, which may be recorded and/or stored in conjunction with a patient consultation, by using a general-use computer. Such a document may be a consultation register, a medical chart, or a medical record.

The display of the health information of the user will now be described in further detail. When the input signal for displaying the health information of the user is input by using the first input unit 110, the web page which represents the health information of the user is displayed on the first display unit 130. The web page is the form used to represent the health information of the user. The health care service provider may care for the health of a plurality of patients. The health care service provider may select a user of the health information terminal 30 desiring to share health-related information from among the plurality of patients, and may refer to the health-related information of the selected user, which is represented in the form of a web page. In an embodiment, the user's health information, which may be previously stored in the DB 170 of the health care device 10, may be displayed on the first display unit 130 in the form of a web page. Alternatively, if the user's health information is stored in an external device, which may be located outside the health care device 10, the user's health information may be provided from the external device by using the health care device 10 and may be displayed on the first display unit 130 in the form of a web page.

As described above, the web page is constructed by using HTML, XHTML, CSS, JavaScript, an image, a flash, or the like, or a combination thereof, and may be provided from a web server. The health care device 10 may include a web application which serves as a web server and provides HTML documents associated with the health information of the user. In another embodiment, a web server may be independent and separate from the health care device 10. In addition, the health care device 10 may display information constructed in the HTML format in the form of a web page by using a web browser, such as, Microsoft Internet Explorer, Mozilla Firefox, Opera, Safari, Chrome, or the like.

The first input unit 110 may be used to input a signal indicating a sharing request from the health care service provider. In further detail, when the signal indicating the sharing request is input via the first input unit 110, data indicating the sharing request is transmitted to the sharing relay device 20 via the first communications interface 120. For example, when the health care service provider selects a sharing request button displayed on the first display unit 130 by using the first input unit 110, the data indicating the sharing request is transmitted to the sharing relay device 20 via the first communications interface 120. The sharing request may include both a sharing-start request and a request for sharing a web page which represents the user's health information.

The first input unit 110 inputs a signal indicating an image generation request from the health care service provider. In further detail, when the signal indicating the image generation request is input by the first input unit 110, the data indicating the image generation request is transmitted to the sharing relay device 20 via the first communications interface

120. For example, when the health care service provider selects an image generation request button displayed on the first display unit 130 by using the first input unit 110, the data indicating the image generation request is transmitted to the sharing relay device 20 via the first communications interface 120.

Alternatively, the data indicating the image generation request may be automatically transmitted to the sharing relay device 20 via the first communications interface 120 by selecting a portion of the web page which is desired to be produced as an image by using the first input unit 110 to select the desired portion of the entirety of the web page displayed on the first display unit 130. For example, when the health care service provider selects a portion which is desired to be shared with the health information terminal 30 from the entirety of the web page displayed on the first display unit 130, using a mouse-dragging method or the like, data indicating a request to produce the selected portion as an image may be transmitted to the sharing relay device 20.

The health care service provider inputs a signal via the first input unit 110 to indicate an emphasized location or a marked location. In further detail, when a signal used to select a point or a portion within the image displayed on the first display unit 130, for example to emphasize or distinctively mark the point or portion, is input by the first input unit 110, the data which indicates position information corresponding to the selected point or portion may be transmitted to the sharing relay device 20 via the first communications interface 120. For example, when the health care service provider selects a portion of the image displayed on the first display unit 130, for example by clicking or dragging (e.g., selecting) the first input unit 110, data that indicates the position information corresponding to the selected portion is transmitted to the sharing relay device 20 via the first communications interface 120.

Although generation of images by web page transformation may be performed in the sharing relay device 20, in another embodiment the health care device 10 may also perform the generation of images by web page transformation.

The first communications interface 120 transmits and receives data to and from the sharing relay device 20 via the network 40. The first communications interface 120 may include a device capable of transmitting and receiving data via the network 40. For example, the first communications interface 120 may be at least one selected from the group consisting of a transmitter, a receiver, a modem, and a transceiver, and the like, and a combination thereof.

The first display unit 130 displays the web page which represents the user's health information, the image desired to be shared, the marked location, and information received from the health information terminal 30 via the sharing relay device 20. The first display unit 130 may include a device capable of displaying visual information. For example, the first display unit 130 may comprise a display, a liquid crystal display ("LCD") screen, a light-emitting diode ("LED"), the monitor of a general-use computer, or the like, or combination thereof.

The memory 140 may include a program memory and a data memory. The program memory stores a program which controls general operations of the health care device 10. The data memory temporarily stores a piece of data which is generated during program execution.

The processor 150 controls an operation of the health care device 10 and an operation for performing the method of sharing an image which represents a user's health information. The processor 150 may be implemented by using an array of a plurality of logic gates, or by using a combination of a general-use micro processor and a memory in which programs executable in the micro processor are stored. The processor 150 may also be implemented by using other types of hardware.

The web application module 160 includes a plurality of web applications which serve as at least one selected from the group consisting of a server and a client in a web environment. The web application module 160 may comprise a plurality of web applications, and may perform its function such that the web applications are stored in the memory 140 and are executed by the processor 150. The web application module 160 includes a web browser, a web server, or the like, or a combination thereof, as further described above.

The health care device 10 may further include an independent application module, and thus the health care device 10 may generate an image by transformation of a web page into the image, transform the resolution of an image, transform position information into standardized position information, encrypt, decrypt, or the like, or a combination thereof.

The DB 170 stores the health information of the user. The health care device 10 stores a piece of health-related information of each of a plurality of users of the health information terminal 30 in the DB 170 in order to care for the health of a plurality of patients. Thus, when the health care service provider refers to the user's health information in the form of a web page, the health information of the user is constructed in an HTML format, or the like, and stored in the DB 170.

When data is transmitted and received between the health care device 10 and the health information terminal 30, the data may not be transmitted and received directly between the health care device 10 and the health information terminal 30, but instead transmitted and/or received via the sharing relay device 20. Independent applications for caring for the health of patients may be installed in the sharing relay device 20 and/or the health information terminal 30. An image sharing function may be added to these independent applications. Thus, a web page representing the health status of a user, which comprises an image, may be shared by using an independent application for caring for the health of a user without using a web application (for example, Active X, or the like) for web page sharing, wherein the web application is one which may be used in the web environment.

Figure 3:
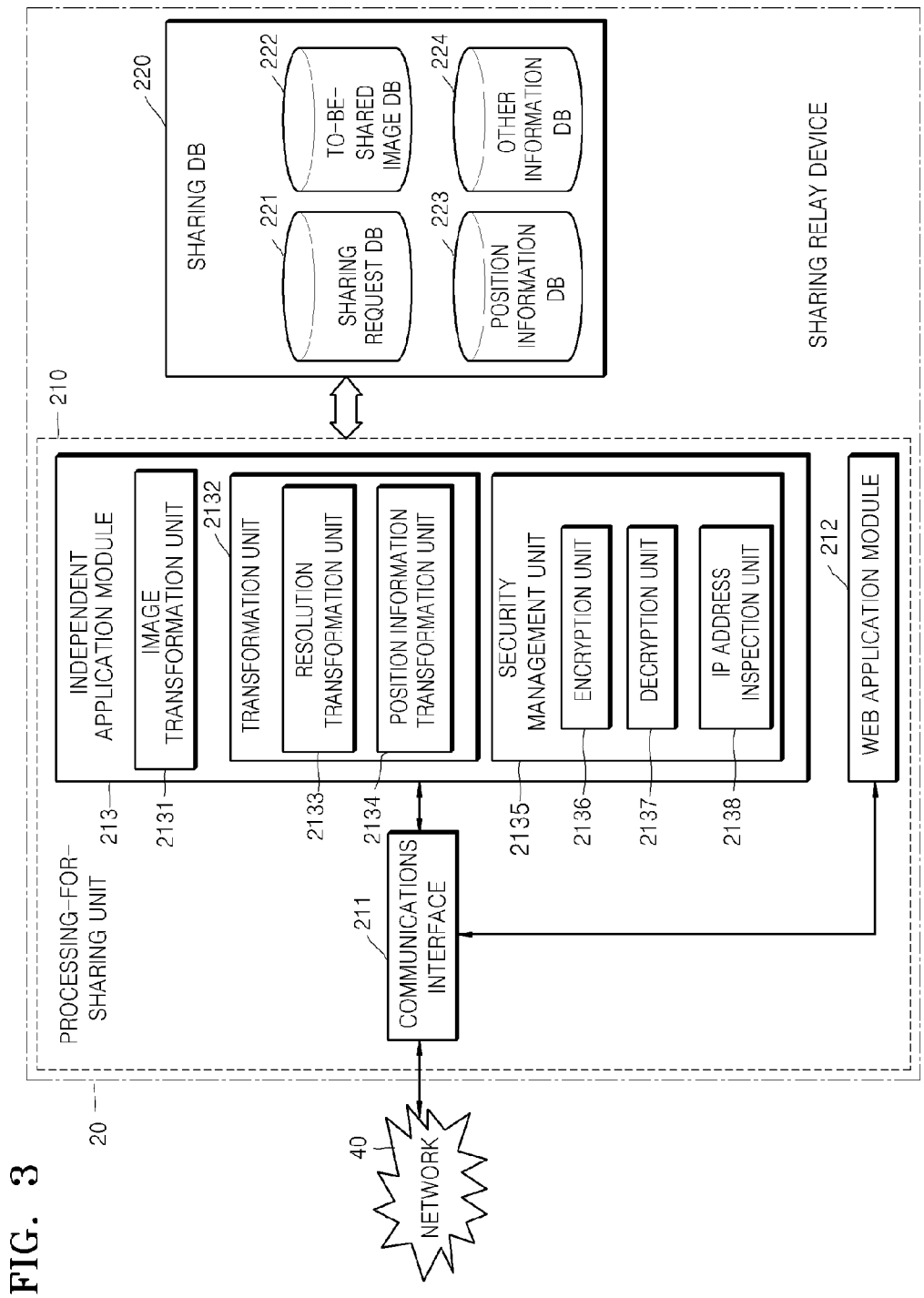
FIG. 3 is a block diagram illustrating a structure of a sharing relay device illustrated in FIG. 2, in further detail.

In an embodiment, the sharing relay device 20 receives data from the health care device 10 via the network 40, transforms a to-be-shared portion of the web page, which represents the user's health information, into an image, stores the image in the sharing DB 220, and transmits the image to the health information terminal 30 via the second communications interface 211. FIG. 3 is a block diagram illustrating an exemplary embodiment of a structure of the sharing relay device 20 illustrated in FIG. 2, in further detail. Referring to FIG. 3, the sharing relay device 20 includes the processing-for-sharing unit 210 and the sharing DB 220.

The processing-for-sharing unit 210 performs data transmission and reception, image transformation to share the web page, which represents the user's health information and may be in the form of an image, between the health care device 10 and the health information terminal 30. Referring to FIG. 3, the processing-for-sharing unit 210 includes the second communications interface 211, the web application module 212, and the first independent application module 213. The first independent application module 213 includes an image transformation unit 2131, a transformation unit 2132, and a security management unit 2135.

The second communications interface 211 receives data from at least one selected from the group consisting of the health care device 10 and the health information terminal 30, and transmits the data to at least one selected from the group consisting of the health care device 10 and the health information terminal 30.

The second communications interface 211 receives data from the health care device 10. The data received from the health care device 10 is at least one selected from the group consisting of sharing-request data, image-generation request data, and position information data about a point or a portion desired to be distinctively marked on the image. In addition, the second communications interface 211 receives an input signal corresponding to a user's input from the health information terminal 30. The second communications interface 211 may transmit information stored in the sharing DB 220 to at least one selected from the group consisting of the health care device 10 and the health information terminal 30, or may transmit received data directly thereto without passing through the sharing DB 220.

As further disclosed above with reference to the first communications interface 120 of the health care device 10, the second communications interface 211 may also include a device capable of transmitting and receiving information via the network 40.

The web application module 212 may include a plurality of web applications, which may serve as a server and/or a client in the web environment. The web application module 212 of the sharing relay device 20 may include a web browser, a web server, and the like, and a combination thereof. The sharing relay device 20 may transmit and receive data to and from the health care device 10 and the health information terminal 30 by using the HTTP, and may read pieces of information which constitute a web page received from the health care device 10, and may transform the web page into an image.

The first independent application module 213 includes at least one application for sharing the web page which represents the health information of the user and is in the form of an image. Referring to FIG. 3, the first independent application module 213 includes the image transformation unit 2131, the transformation unit 2132, and the security management unit 2135. The transformation unit 2132 includes a resolution transformation unit 2133 and a position information transformation unit 2134. The security management unit 2135 includes an encryption unit 2136, a decryption unit 2137, and an IP address inspection unit 2138. The at least one application which constitutes the first independent application module 213 may be stored in a memory (not shown) and executed by a processor (not shown).

The first independent application module 213 performs a function, which may be performed in the sharing relay device 20, to allow the health care device 10 and the health information terminal 30 to share health information. In another embodiment, if a function of the first independent application module 213 is performed in the health care device 10 as further disclosed above, the sharing relay device 20 may not perform the function of the first independent application module 213.

The image transformation unit 2131 may transform the web page representing the user's health information into an image. In further detail, the image transformation unit 2131 transforms a web page representing the user's health information, which is to be shared with the health information terminal 30, into an image, and stores the image in the sharing DB 220. The transformation of the web page into the image denotes transformation of a portion to be shared with the health information terminal 30, of an entirety of the web page representing the user's health information, which is displayed on the first display unit 130 of the health care device 10. Accordingly, the image transformation unit 2131 may transform a portion of the web page which includes the user's health information into an image file, and in turn the image file may correspond to an image which represents the health information of the user.

A capture function may be used to transform the portion of the web page into the image. The capture function denotes transforming the portion of the web page displayed on the first display unit 130 of the health care device 10 into an image file and storing the image file. Based on information representing the web page provided by the health care device 10 and information about the portion to be shared, the image transformation unit 2131 may interpret the pieces of information as the web page, capture the to-be-shared portion from the web page, and store the captured image in a to-be-shared image DB 222. In an embodiment, the web page may be interpreted by the web application module 212 by using data received from the health care device 10 and be displayed. Alternatively, the sharing relay device 20 may interpret HTML which was used to construct the web page, capture the to-be-shared portion from the web page on the basis of the result of the interpretation, and transform the captured portion into an image, without visually displaying the web page.

The image file may have a format such as Graphic Interchange Format ("GIF"), Joint Photographic Coding Experts Group ("JPEG"), Tagged Image File Format ("TIFF"), PhotoShop Document ("PSD"), BitMap ("BMP"), Encapsulated PostScript ("EPS"), Truevision Graphics Adapter ("TGA"), Computer Graphics Metafile ("CGM"), Windows Metafile ("WMF"), Portable Document Format ("PDF"), Portable Network Graphics ("PNG"), or the like, according to a compression method or a storing method. The format of the image file is not limited thereto and may be any format capable of representing an image.

The image transformation unit 2131 transforms the captured web page into an image file. The image file corresponds to an image which represents the health information of the user. The capturing may be controlled by the health care device 10. For example, if the health care service provider selects a portion which is desired to be shared with the health information terminal 30 from the entirety of the web page displayed on the first display unit 130 of the health care device 10, the selected portion is captured by the image transformation unit 2131. The captured part is transformed into the image which represents the user's health information. Position information about the selected portion which is desired to be shared may be transmitted to the sharing relay device 20 and the position information may serve as information about the selected portion. Alternatively, only information about a structure of a web page corresponding to the selected portion may be transmitted to the sharing relay device 20 and the information may serve as the information about the selected portion.

The sharing relay device 20 receives pieces of data, which constitute the web page representing the user's health information, from the health care device 10, transforms the web page into an image file on the basis of the received pieces of data, and stores the image file in the sharing DB 220. The image transformation unit 2131 transmits the image representing the user's health information, which has been generated according to the above-described method, to at least one selected from the group consisting of the sharing DB 220, the transformation unit 2132, and the security management unit 2135.

The transformation unit 2132 transforms characteristics of the image generated by the image transformation unit 2131 and characteristics of position information about a point or a portion on an image received via the second communications interface 211. Referring to FIG. 3, the transformation unit 2132 includes the resolution transformation unit 2133 and the position information transformation unit 2134.

The resolution transformation unit 2133 transforms the characteristics of the image representing the user's health information, which has been generated by the image transformation unit 2131, into standard characteristics. The characteristics of the image correspond to a standard for displaying an image on a screen, for example, a resolution. The resolution represents how many pixels or dots are used to express an image, and thus corresponds to an index which indicates the precision of the image. Resolution may be classified into a pixel resolution, an image resolution, and a monitor resolution, and the resolution may include at least one of the above-described resolutions.

The pixel resolution is also referred to as a bit resolution and denotes the number of colors used in producing a single pixel. For example, if the pixel resolution is 1 bit, information contained in a pixel is displayed in black and white. If the pixel resolution is 8 bits, information contained in a pixel is displayed using 256 colors, i.e., $2^8$. If the pixel resolution is 24 bits, information included in a pixel is displayed using 16,777,216 colors, i.e., $2^{24}$.

The image resolution denotes how many pixels constitute a single image. For example, if an image is 72 pixels per inch ("ppi") (or 72 dots per inch, "dpi"), the image is made up of a total of 5,184 dots or pixels, i.e., 72 dots in a 1-inch width and 72 dots in a 1-inch length.

The monitor resolution denotes how many pixels are included in a single screen, and is expressed in the formula of a multiplication of the number of pixels in the width and the number of pixels in the length. For example, 1024×768 denotes representation of an image that is 1024 pixels wide and 768 pixels long on a monitor. Examples of the monitor resolution may include, 1280×1024, 1280×960, 1152×864, 1024×768, 800×600, or the like.

The resolution transformation unit 2133 transforms the resolution of the image representing the user's health information and generated by the image transformation unit 2131 into a standard resolution. The standard resolution may not be related to the resolution of the health care device 10 and the health information terminal 30 and may be set according to an agreement between two of the group consisting of the health care device 10, the sharing relay device 20, and the health information terminal 30. When a plurality of health care service providers share images representing the user's health information with a plurality of health information terminals 30 by using the health care device 10, each of the health information terminals 30 may have a different resolution. Although the health information terminals 30 may each have a different resolution, a single standard resolution may be selected to provide efficient image sharing, and the sharing relay device 20 may transform the resolution of all of the images into the selected standard resolution. Because the images received by the health information terminals 30 have the standard resolution, the standard resolution may be transformed into a resolution suitable for the health information terminals 30, or the received images may be displayed with the standard resolution.

For example, the image generated by the image transformation unit 2131 may have a resolution selected based on the characteristics of the sharing relay device 20. Alternatively, if the health care device 10 includes an independent application module and generates an image, the generated image may have a resolution selected based on the characteristics of the health care device 10. If the resolution of the health information terminal 30 is different from that of the health care device 10 or the sharing relay device 20, a portion of an image which is shared may be destroyed or may be cut off. Accordingly, the resolution transformation unit 2133 transforms the resolution of the image into a standard resolution, and the health information terminal 30 transforms the standard resolution to the resolution of the health information terminal 30, thereby sharing the image without degrading (e.g., damaging) the image. A method of transforming the resolution of an image is known to one of ordinary skill in the art and can be executed without undue experimentation, and thus a detailed description thereof will be omitted.

The position information transformation unit 2134 transforms position information about a point or a portion on the image displayed on the first display unit 130 of the health care device 10 into standard position information. As further disclosed above, the position information about the point or portion selected by the first input unit 110 of the health care device 10 from the image displayed on the first display unit 130 is transmitted to the sharing relay device 20, and the position information transformation unit 2134 normalizes the received position information to generate the standard position information. At this time, the entirety or a portion of the image displayed on the first display unit 130 of the health care device 10 may be shared with the health information terminal 30, and the point or portion may be selected by the health care service provider by using the first input unit 110 of the health care device 10. For example, the health care service provider may select a point or portion to be emphasized or distinctively marked from the image to be shared, by using the first input unit 110. The selection of the point may be performed by selecting (e.g., clicking or dragging a mouse), which is an example of the first input unit 110.

The position information about the point or portion includes position information depending on the characteristics of the first display unit 130 of the health care device 10. For example, the position information about the point or portion may be represented as position information depending on the resolution of the first display unit 130 of the health care device 10. In an embodiment, the position information about the point or portion may include coordinates. If only a portion of the image displayed on the first display unit 130 of the health care device 10 is shared with the health information terminal 30, respective positions on the health care device 10 and the health information terminal 30 indicated by the position information about the point or portion may differ from each other according to which point or portion is selected. Accordingly, if position information unique to the health care device 10 is a relative coordinate, the position information transformation unit 2134 may normalize the relative coordinate into a standard coordinate which is not related to the characteristics of the health care device 10 or the health information terminal 30.

In further detail, the position information transformation unit 2134 may transform a relative coordinate of position information into a standard coordinate. The transformation of the relative coordinate into the standard coordinate may be performed by normalizing the coordinate of the point or portion selected by the first input unit 110 of the health care device 10 into the standard coordinate. For example, a point existing on both the health care device 10 and the health information terminal 30 from an image shared between the health care device 10 and the health information terminal 30 may be selected as a base point, and a coordinate may be selected based on the selected base point. For convenience of explanation, a portion selected (e.g., clicked) by the health care service provider by using the first input unit 110 of the health care device 10 is referred as a marked position.

Figure 4:
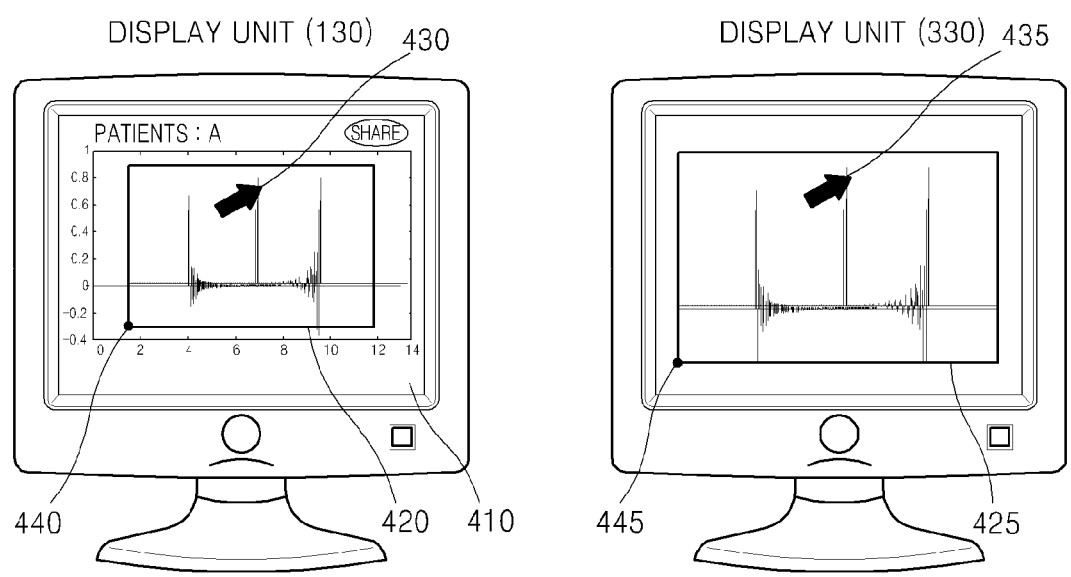
FIG. 4 illustrates an exemplary embodiment of transformation of position information performed by a position information transformation unit included in the health information image sharing system illustrated in FIGS. 1 and 2.

FIG. 4 illustrates an exemplary embodiment of transformation of the position information performed by the position information transformation unit 2134. Referring to FIG. 4, a web page 410 which represents the health information of a user, a to-be-shared portion 420, a marked position 430, and a first base point 440 are displayed on the first display unit 130 of the health care device 10, and a to-be-shared image 425, a marked position 435, and a second base point 445 are displayed on the second display unit 330 of the health information terminal 30.

The web page 410 representing the user's health information is displayed on the first display unit 130 of the health care device 10, and a portion to be shared with the health information terminal 30 from the entirety of the web page 410 is selected through the first input unit 110 of the health care device 10. The selected portion may be displayed as the to-be-shared portion 420, and the to-be-shared portion may be displayed on the second display unit 330 of the health information terminal 30 via the sharing relay device 20. If the marked position 430 is selected using the first input unit 110 of the health care device 10, position information about the marked position 430 is transformed into a standard coordinate by the position information transformation unit 2134 and then the standard coordinate is stored in the sharing DB 220. In the transformation of the position information about the marked position 430 into the standard coordinate, a point existing on both the to-be-shared portion 420 and the to-be-shared image 425 is set as a base point. For example, a base point existing on both to-be-shared portions on the health care device 10 and the health information terminal 30 may be set (e.g., selected), a coordinate may be calculated from the base point, and the calculated coordinate may be transmitted to the health information terminal 30 via the sharing relay device 20. A lowest point on the left side of the to-be-shared portion 420 displayed on the health care device 10 is set as the first base point 440, and a coordinate of the mark position 430 in relation to the first base point 440 is calculated. The health information terminal 30 may receive the calculated coordinate, set a lowest point on the left side of the to-be-shared image 425 displayed on the health information terminal 30 to be the second base point 445, and indicate as the marked position 435 a point corresponding to a coordinate calculated from the second base point 445.

Due to this transformation of the characteristics of position information in the position information transformation unit 2134, marking positions at different locations on the health care device 10 and the health information terminal 30 due to the characteristics (for example, a resolution) related to image display and a portion to be shared may be substantially reduced or effectively eliminated. This transformation of the characteristics of position information one example of the transformation of the position information. In another embodiment, the position information may be transformed according to another method which can be selected by one of ordinary skill in the art without undue experimentation.

Referring back to FIG. 3, the transformation unit 2132 transforms the characteristics of the image generated by the image transformation unit 2131 and transforms the characteristics of the position information about the point or portion on the image received from the health care device 10. The transformation unit 2132 may be included in at least one selected from the group consisting of the health care device 10 and the sharing relay device 20. Thus, if a transformation is performed in the health care device 10, the resolution transformation and the position information transformation may be performed not only in the sharing relay device 20 but also in the health care device 10.

The security management unit 2135 decrypts encrypted information received from the health information terminal 30 and encrypts information to be transmitted to the health information terminal 30. Referring to FIG. 3, in an embodiment, the security management unit 2135 includes the encryption unit 2136, the decryption unit 2137, and the IP address inspection unit 2138. The security management unit 2135 encrypts or decrypts transmitted and received information by using symmetric key cryptography, asymmetric key cryptography, or the like, or a combination thereof.

The encryption unit 2136 encrypts at least one selected from the group consisting of an image generated by the image transformation unit 2131, an image whose resolution has been transformed by the resolution transformation unit 2133, position information transformed by the position information transformation unit 2134, and pieces of information received from the health care device 10, by using a symmetric key, a public key, or the like, or combination thereof according to the type of cryptographic system used. Information encrypted by the encryption unit 2136 is stored in the sharing DB 220 or transmitted to the health care device 10 and the health information terminal 30 via the second communications interface 211.

The decryption unit 2137 decrypts encrypted information received from the health information terminal 30 and the health care device 10, by using a symmetric key, a public key, or the like, or a combination thereof, according to the type of cryptographic system used. When data received via the second communications interface 211 is encrypted, the received data is transmitted to and decrypted by the decryption unit 2137. The information decrypted by the decryption unit 2137 is stored in the sharing DB 220 or transmitted to the health care device 10 and the health information terminal 30 via the second communications interface 211.

Encryption and decryption are performed according to an encryption algorithm and a decryption algorithm which depend on the type of cryptographic system used, as can be determined by one of ordinary skill in the art without undue experimentation, and thus a detailed description thereof will be omitted. The symmetric key cryptography and the asymmetric key cryptography are examples of the cryptographic system, and the encryption and decryption are not limited thereto. In other words, the encryption or decryption may be performed using a method capable of transforming original information into a non-understandable form or retransforming the information in the non-understandable form into the original information.

An encryption key and a decryption key may be stored according to a setting between the health care device 10, the sharing relay device 20, and the health information terminal 30 or may be received from an authentication device.

The IP address inspection unit 2138 inspects an IP address of the health information terminal 30 which requests data transmission. Only when the IP address of the health information terminal 30 which requests data transmission is identical to an IP address of the health information terminal 30 which has been previously stored in the sharing relay device 20, is data transmitted to the health information terminal 30.

For example, if health information terminals 30 of users are initially connected to the sharing relay device 20, the sharing relay device 20 stores the IP addresses of the health information terminals 30. When a data transmission request for downloading an image that represents a user's health information is received from the health information terminal 30, the IP address inspection unit 2138 inspects the IP address of the health information terminal 30. Only when the IP address is identical to a stored IP address, is data transmitted via the second communications interface 211. The health information of the user may be private, and thus may be desirably kept confidential. Generally, the user transmits and receives data by using his or her own health information terminal 30, and thus if the health information terminal 30 has a unique IP address, communication security of health information may be ensured.

The encryption unit 2136 and the decryption unit 2137 of the security management unit 2135 may exist in at least one selected from the group consisting of the health care device 10 and the sharing relay device 20. Accordingly, if a security managing function is performed in the health care device 10, the above-described encryption and decryption may not be performed in the sharing relay device 20 but instead, may be performed in the health care device 10.

Since a to-be-shared image representing the user's health information is encrypted by the security management unit 2135 and transmitted via a public network such as the Internet, communication security between the health care device 10 and the health information terminal 30 is substantially ensured.

The sharing DB 220 stores data received from at least one of the health care device 10, the health information terminal 30, and pieces of information generated by the image transformation unit 2131, the transformation unit 2132, and the security management unit 2135. Referring to FIG. 3, in an embodiment the sharing DB 220 includes a sharing request DB 221, the to-be-shared image DB 222, a position information DB 223, and an other information DB 224. The other information DB 224 may be a DB for storing information other than the position information. The sharing DB 220 may further include a program memory (not shown) and a data memory (not shown) in addition to the above-described DBs which are illustrated as storage media. As further described above, the program memory stores a program for controlling a general operation of the sharing relay device 20, and the data memory temporarily stores pieces of data generated during program execution.

The sharing request DB 221 stores data indicating a sharing request received from the health care device 10. In the sharing request, when a signal indicating the sharing request is received through the first input unit 110 of the health care device 10, the data which indicates the sharing request is received via the second communications interface 211 and stored in the sharing request DB 221.

The to-be-shared image DB 222 stores at least one selected from the group consisting of a to-be-shared image generated by the image transformation unit 2131, a transformed to-be-shared image obtained by the resolution transformation unit 2133, an encrypted to-be-shared image obtained by the encryption unit 2136, and a decrypted to-be-shared image obtained by the decryption unit 2137.

The image generated by the image transformation unit 2131 may be encrypted by the encryption unit 2136 and then stored in the to-be-shared image DB 222. Alternatively, the image generated by the image transformation unit 2131 may be transformed into an image with a standard resolution by the resolution transformation unit 2133 and then stored in the to-be-shared image DB 222.

The position information DB 223 stores position information about a point or a portion on the to-be-shared image received from the health care device 10. The position information about the point or portion on the to-be-shared image may be one selected from the group consisting of information about a point or a portion on a to-be-shared image input by the first input unit 110 of the health care device 10, position information transformed by the position information transformation unit 2134, position information encrypted by the encryption unit 2136, position information decrypted by the decryption unit 2137, and the like, and a combination thereof.

The other information DB 224 stores data received from the health information terminal 30. When information other than the sharing request, the to-be-shared image, and the position information is desired to be transmitted and received, the other information may be stored in the other information DB 224. When information to be transmitted to the health care device 10 is input by the second input unit 320 of the health information terminal 30, the second communications interface 211 receives the input information, and the received information may be stored in the other information DB 224.

The sharing relay device 20 stores the image and information about the marked position which is to be shared between the health care device 10 and the health information terminal 30 in at least one of the DBs included in the sharing DB 220. Thus, in contrast with sharing of a screen by using only a web application in the web environment of a general-use computer, the health information image sharing system illustrated in FIGS. 1 through 3 may ensure real-time sharing without increasing the load on a server.

Figure 5:
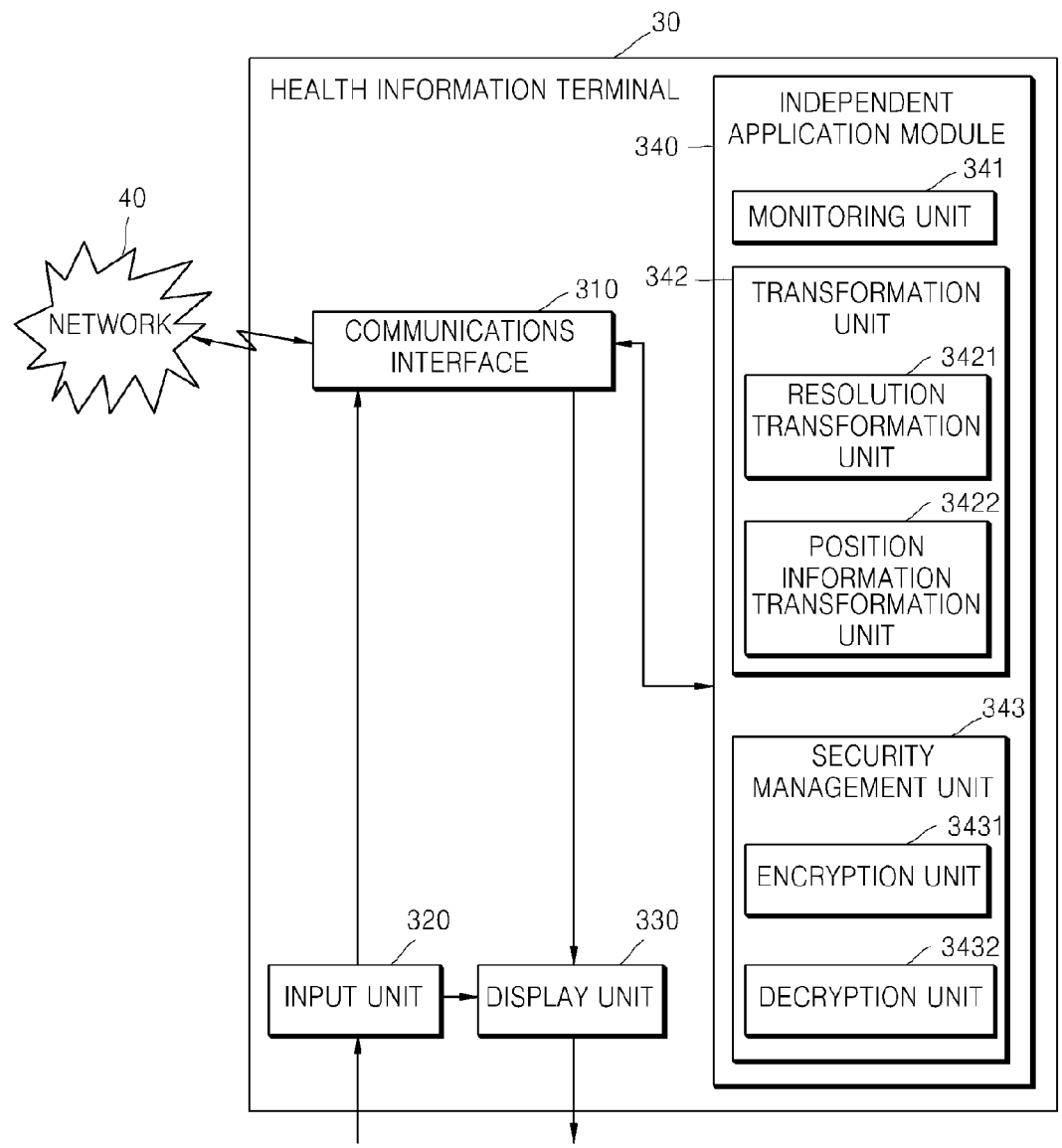
FIG. 5 is a block diagram illustrating a structure of a health information terminal illustrated in FIG. 2, in further detail.

Referring back to FIG. 2, in an embodiment the health information terminal 30 monitors the sharing relay device 20, and if it is determined from the monitoring that a sharing request for health information exists, the health information terminal 30 downloads a to-be-shared image from the sharing relay device 20 and displays the downloaded image. FIG. 5 is a block diagram illustrating an exemplary embodiment of a structure of the health information terminal 30 illustrated in FIG. 2, in further detail. Referring to FIG. 5, the health information terminal 30 includes a third communications interface 310, a second input unit 320, a second display unit 330, and a second independent application module 340.

The third communications interface 310 transmits and receives data with the sharing relay device 20 via the network 40. The third communications interface 310 includes all devices capable of transmitting and receiving information via the network 40. For example, the third communications interface 310 is at least one of a transmitter, a receiver, a modem, a transceiver, or the like, or a combination thereof.

The third communications interface 310 transmits an input signal corresponding to a user's input to the health care device 10 via the sharing relay device 20. The health information terminal 30 receives the input signal via the second input unit 320. The input signal includes at least one of information about the health of a user, information about inquiries of the user, a health care schedule of the user, and position information about a point or a portion on an image displayed on the health information terminal 30 of the user.

For example, when the content of inquiries of a user, position information representing a selection of a point or a portion on a shared image, or the like is received via the second input unit 320, the received information may be transmitted to the sharing relay device 20. The transmitted information may be received via the second communications interface 211 of the sharing relay device 20 and stored in the other information DB 224. The stored information may be transmitted to the health care device 10 via the second communications interface 211 of the sharing relay device 20.

The third communications interface 310 receives at least one selected from the group consisting of data indicating a sharing request, data indicating a to-be-shared image, and data indicating position information from the sharing relay device 20 via the network 40, and transmits a user's input to the sharing relay device 20.

The second input unit 320 is used to input a signal from the user of the health information terminal 30. As further described above, the input signal includes at least one of information about the health of the user, information about inquiries of the user, a health care schedule of the user, and position information about a point or a portion on an image displayed on the health information terminal 30 of the user. The second input unit 320 includes all devices for inputting a signal from the user of the health information terminal 30. For example, the second input unit 320 includes a keyboard, a mouse, a touch pad, an audio recognition device, or the like, or a combination thereof.

The second display unit 330 displays an image that represents the health information of the user, and overlays a mark on the displayed image. The second display unit 330 displays a to-be-shared image received via the third communications interface 310, or a to-be-shared image whose resolution has been transformed to conform to the characteristics of the health information terminal 30 by the resolution transformation unit 3421, or a to-be-shared image decrypted by the decryption unit 3432 if data representing the received to-be-shared image has been encrypted.

When the data indicating the position information is received from the sharing relay device 20, a mark is overlaid on a location corresponding to a position indicated by the position information. Alternatively, the data indicating the position information may be transformed by the position information transformation unit 3422 and may conform to the characteristics of the health information terminal 30 and a mark is overlaid on a location corresponding to the transformed data. Alternatively, if the received data indicating the position information has been encrypted, a mark may be overlaid on a location corresponding to a result of decryption, performed by the decryption unit 3432, on the data indicating the position information.

The overlay denotes display of a mark over an image displayed on the second display unit 330, the mark being distinguishable from the displayed image. The mark may be an arrow, a circle, a polygon-shaped box, a sphere, or the like. For example, when the health care service provider selects a portion of the to-be-shared image by using the health care device 10, a mark is displayed over the selected portion of the to-be-shared image displayed on the second display unit 330 of the health information terminal 30.

The display of a mark over the to-be-shared image displayed on the second display unit 330 of the health information terminal 30 when the health care service provider selects a portion from the to-be-shared image is an example. In an embodiment, the entire image on which the selected part is displayed may be captured and shared again, or a stream of data, instead of a captured image, may be transmitted and shared with the health information terminal 30.

The second display unit 330 displays the to-be-shared image, the marked position, or the like, or a combination thereof. The second display unit 330 includes a device for displaying visual information. For example, the second display unit 330 may be a display, an LCD screen, an LED, a monitor, or the like.

The second independent application module 340 may perform a function which may be performed in the health information terminal 30 to share the health information between the health care device 10 and the health information terminal 30. The second independent application module 340 may be comprise a plurality of applications and perform a function in such a way that the applications are stored in a memory (not shown) and executed by a processor (not shown). Referring to FIG. 5, in an embodiment, the second independent application module 340 includes a monitoring unit 341, a transformation unit 342, and a security management unit 343.

The monitoring unit 341 monitors if a sharing request for the health information of the user is made by the sharing relay device 20 which provides the web page representing the user's health information in the form of an image. The monitoring unit 341 of the health information terminal 30 monitors the sharing relay device 20 via the third communications interface 310. The sharing request is transmitted from the health care device 10 to the sharing relay device 20, and when the sharing request is received from the sharing relay device 20, the monitoring unit 341 requests the sharing relay device 20 to transmit data in order to download an image to be captured from the web page.

The monitoring unit 341 transmits a data transmission request (for example, an HTTP request) to the sharing relay device 20 via the third communications interface 310 in order to receive at least one selected from the group consisting of sharing-request data, to-be-shared image data, position information data, and the like, which are stored in the sharing relay device 20. In response to the data transmission request, the pieces of data stored in the sharing DB 220 of the sharing relay device 20 may be received via the third communications interface 310.

The monitoring unit 341 monitors the sharing relay device 20. In an embodiment, the monitoring unit 341 repeatedly transmits the data transmission request to the sharing relay device 20 via the third communications interface 310. When data indicating the sharing request is received by the sharing relay device 20 from the health care device 10, the third communications interface 310 downloads the to-be-shared image stored in the sharing relay device 20 from the sharing relay device 20 in response to the data transmission request.

The monitoring unit 341 occasionally or periodically monitors the sharing relay device 20. In an embodiment, when the data indicating the sharing request is received by the sharing relay device 20 from the health care device 10, the sharing relay device 20 stores the received data in the sharing request DB 221. The monitoring unit 341 monitors the sharing relay device 20 by periodically transmitting the data transmission request. When the data indicating the sharing request is stored in the sharing request DB 221 of the sharing relay device 20, it is inquired of the user of the health information terminal 30 whether the health care device 10 and the health information terminal 30 share an image, and then image sharing starts. Alternatively, image sharing starts automatically without inquiry of the user.

When the image sharing between the health care device 10 and the health information terminal 30 starts, the monitoring unit 341 increases the number of times monitoring is performed. For example, in an embodiment wherein an image sharing starts while the monitoring unit 341 is transmitting a data transmission request to the sharing relay device 20 every one minute, the monitoring unit 341 may increase the number of data transmission requests made to the number of times a data transmission request is made to a request every 30 seconds.

The number of times monitoring is performed may increase or decrease according to information representing the user's health care schedule stored in the health information terminal 30. For example, if image sharing between the health information terminal 30 and the health care device 10 is scheduled by both the health care device 10 and the health information terminal 30 (for example, on the day and time scheduled for a consultation between the health care service provider and the user), the number of data transmission requests made on the agreed day and time may be set to further increase.

When the image sharing between the health care device 10 and the health information terminal 30 starts, in general, data transmission and reception between the health care device 10 and the health information terminal 30 may occur with greater frequency. Accordingly, when the image sharing between the health care device 10 and the health information terminal 30 starts, the monitoring unit may 341 increase the number of monitoring operations performed, thereby ensuring real-time information sharing between the health care device 10 and the health information terminal 30.

The monitoring unit 341 requests the sharing relay device 20 to transmit data via the third communications interface 310, and thus the sharing relay device 20 transmits data representing the to-be-shared image stored in the to-be-shared image DB 222 and data indicating the position information stored in the position information DB 223 to the health information terminal 30.

The monitoring unit 341 monitors the sharing relay device 20. If it is determined by the monitoring that there exists a sharing request for the health information of the user, the third communications interface 310 downloads an image captured from the web page representing the user's health information from the sharing relay device 20. In an embodiment, the third communications interface 310 downloads the captured to-be-shared image stored in the to-be-shared image DB 222 of the sharing relay device 20.

The monitoring unit 341 may continuously monitor the sharing relay device 20 while connection between the health information terminal 30 and the sharing relay device 20 is maintained. When a new image about the health information of the user is provided from the sharing relay device 20, the third communications interface 310 may download the new image from the sharing relay device 20 and the downloaded image may be displayed on the second display unit 330. The new image may be partially overlaid on the image previously displayed on the second display unit 330, or only the new image may be displayed on the second display unit 330. In other words, when a sharing request for a new image representing the health information of the user is made by the health care device 10, real-time sharing with the health information terminal 30 may be ensured due to the monitoring performed by the monitoring unit 341.

Real-time characteristics of images and position information may be substantially ensured due to the increase in the number of monitoring operations performed. In addition, the stateless feature of the HTTP may be compensated for by receiving pieces of data stored in the sharing DB 220 of the sharing relay device 20. For example, while the health care service provider is referring to a web page representing information about the blood pressure of the user, the health care service provider may share a portion of the web page with the user of the health information terminal 30 by using the health care device 10. Furthermore, when the health care service provider desires to indicate a portion of the shared image, the indicated portion may be displayed on the same location on the health information terminal 30 during an interval of an extremely short period of time, because sharing is performed in real time.

The transformation unit 342 transforms characteristics of a to-be-shared image received from the sharing relay device 20, and transforms characteristics of position information about a point or a portion on the to-be-shared image received from the sharing relay device 20. Referring to FIG. 5, in an embodiment, the transformation unit 342 includes a resolution transformation unit 3421 and a position information transformation unit 3422.

The resolution transformation unit 3421 transforms the characteristics of an image representing the user's health information, which has been received from the sharing relay device 20, into characteristics unique to the health information terminal 30. The characteristics of the image correspond to a resolution for displaying an image on a screen. If the resolution of the to-be-shared image has been transformed into a standard resolution in the health care device 10 or the sharing relay device 20, the to-be-shared image having the standard resolution may be retransformed into an image having a resolution unique to the health information terminal 30. An image transforming method has been further described above with reference to the resolution transformation unit 2133 of the sharing relay device 20, and thus an additional detailed description thereof will be omitted.

The position information transformation unit 3422 transforms position information about a point or a portion on the to-be-shared image into position information unique to the health information terminal 30. The to-be-shared image is an image to be shared between the health care device 10 and the health information terminal 30. The position information transformation unit 3422 transforms position information set as a standard coordinate in at least one selected from the group consisting of the health care device 10 and the sharing relay device 20 or position information received through the sharing relay device 20 into the position information unique to the health information terminal 30. A method of transforming the position information has been further described above in detail with reference to the position information transformation unit 2134 of the sharing relay device 20, and thus an additional detailed description thereof will be omitted.

The security management unit 343 decrypts encrypted information received from the sharing relay device 20 and encrypts information to be transmitted to the sharing relay device 20. Referring to FIG. 5, in an embodiment the security management unit 343 includes an encryption unit 3431 and a decryption unit 3432.

The encryption unit 3431 encrypts the information to be transmitted to the sharing relay device 20, by using a symmetric key, a public key, or the like, or a combination thereof of the health information terminal 30 according to the type of cryptographic system. The second input unit 320 of the health information terminal 30 is used to input a signal, the encryption unit 3431 encrypts the input signal, and the third communications interface 310 transmits a result of the encryption to the sharing relay device 20.

The decryption unit 3432 decrypts the encrypted information received from the sharing relay device 20, by using a symmetric key or a secret key of the sharing relay device 20 according to the type of cryptographic system used. If information received from the sharing relay device 20 is encrypted information, the received information is transmitted to and decrypted by the decryption unit 3432.

Encryption and decryption methods have been further described above in detail with reference to the security management unit 2135 of the sharing relay device 20, and thus a detailed description thereof will be omitted.

The health care device 10, the sharing relay device 20, and the health information terminal 30 may include a single processor or a plurality of processors. Alternatively, each of components of the health care device 10, the sharing relay device 20, and the health information terminal 30 may correspond to a single processor or a plurality of processors. The processor may be implemented using an array of logic gates, or by combining a general-use microprocessor and a memory in which programs executable in the microprocessor are stored. It will be understood by one of ordinary skill in the art that the processor may also be implemented using other types of hardware without undue experimentation.

The health information image sharing system may effectively share an image representing the health information of a patient, for example, a medical record or the like, in tele-medicine. When the health care service provider selects a point or a portion desired to be emphasized or indicated, the selected point or portion may be shared in real time, and thus a medical service corresponding to tele-medicine, which appears to have the same immediate effect as a physical consultation between a doctor and a patient, may be provided.

Figure 6:
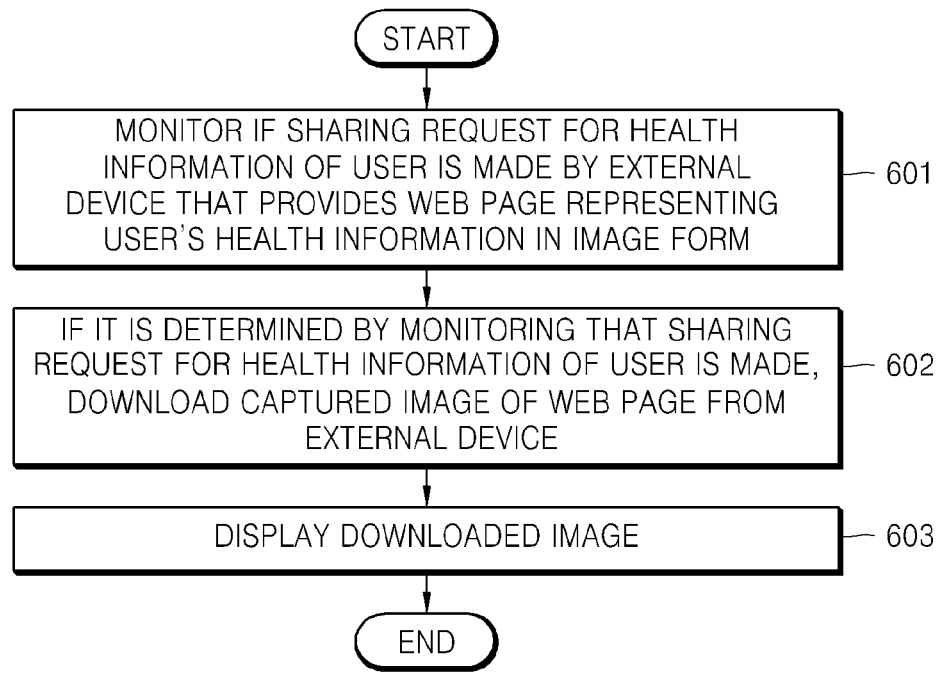
FIG. 6 is a flowchart illustrating an exemplary embodiment of a method in which the health information of a user is displayed on the health information terminal included in the health information image sharing system illustrated in FIG. 1.

FIG. 6 is a flowchart illustrating an exemplary embodiment of a method in which the health information of a user is displayed on the health information terminal 30 illustrated in FIG. 5. Referring to FIG. 6, the method of displaying a user's health information includes operations which may be sequentially performed in the health information terminal 30 illustrated in FIG. 5. The description of the health information terminal 30 of FIG. 5, although hereinafter omitted, may also be applied to the method of displaying a user's health information.

In operation 601, the monitoring unit 341 monitors if a sharing request for the health information of the user is made by an external device which provides a web page representing the user's health information in the form of an image. The external device is at least one selected from the group consisting of the sharing relay device 20 and the health care device 10.

In operation 602, if it is determined by monitoring that a sharing request for the health information of the user is made, the third communications interface 310 downloads a captured image of the web page from the external device. The health information terminal 30 transmits a data transmission request to the external device. In response to the data transmission request, the external device transmits the web page in an image form to the health information terminal 30. In an embodiment, when a to-be-shared image is stored in the sharing relay device 20 at the request of the health care device 10, the health information terminal 30 receives the to-be-shared image from the sharing relay device 20.

In operation 603, the second display unit 330 displays the downloaded image.

Figure 7:
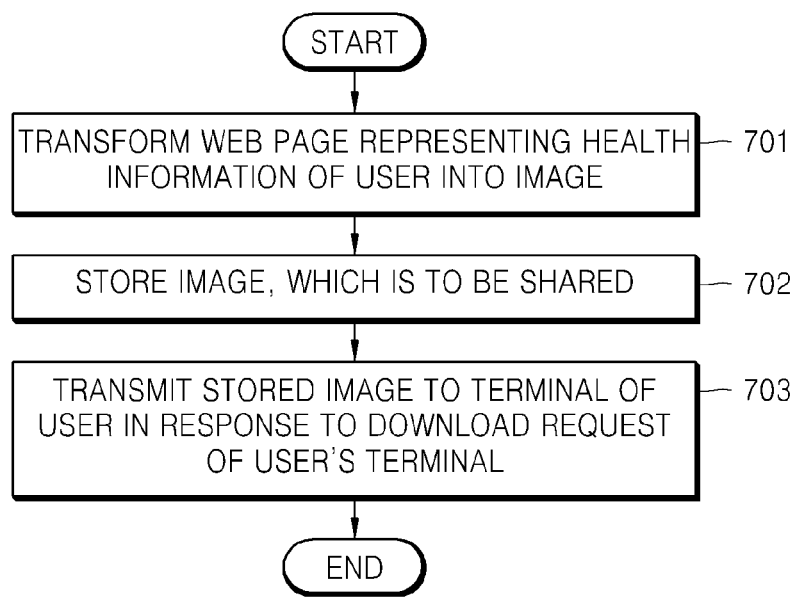
FIG. 7 is a flowchart illustrating an exemplary embodiment of a method in which the sharing relay device illustrated in FIGS. 1 through 3 provides the health information of a user in the form of an image.

FIG. 7 is a flowchart illustrating an exemplary embodiment of a method in which the sharing relay device 20 illustrated in FIG. 3 provides the health information of a user in the form of an image. Referring to FIG. 7, the user's health information providing method includes operations which may be sequentially performed in the sharing relay device 20. Accordingly, the description of the sharing relay device 20 of FIG. 3, although hereinafter omitted, may also be applied to the user's health information providing method.

In operation 701, the image transformation unit 2131 transforms a web page representing the health information of the user into an image in response to a request of the health care device 10. The image transformation may be performed using a method of capturing a portion to be shared from a web page.

In operation 702, the image, which is to be shared, is stored in the sharing DB 220. The to-be-shared image may be stored in the to-be-shared image DB 222.

In operation 703, the second communications interface 211 transmits the image stored in the sharing DB 220 to a terminal of the user in response to a download request of the user's terminal. The user's terminal may be the health information terminal 30 of the user.

FIG. 8 is a data flow diagram illustrating an exemplary embodiment wherein the health care device 10, the sharing relay device 20, and the health information terminal 30 share a health information image.

In operation 801, the health information terminal 30 monitors the sharing relay device 20. The monitoring may be performed by transmitting an HTTP request to the sharing relay device 20.

In operation 802, the sharing relay device 20 transmits to the health information terminal 30 a signal, which indicates that no data has been received from the health care device 10. The sharing relay device 20 may transmit a signal to the health information terminal 30, wherein the signal indicates that no data has been received from the health care device 10, in response to an HTTP request of the health information terminal 30.

Operations 803 and 804 correspond to a repetition of operations 801 and 802. In an embodiment, the health information terminal 30 may periodically or randomly monitor the sharing relay device 20.

In operation 805, the health care device 10 transmits a request to share the health information of the user to the sharing relay device 20.

In operation 806, the health information terminal 30 monitors the sharing relay device 20.

In operation 807, the sharing relay device 20 transmits to the health information terminal 30 a signal which indicates that a sharing request has been made by the health care device 10, in response to the monitoring of the health information terminal 30.

In operation 808, the health information terminal 30 transmits data indicating the start of sharing to the sharing relay device 20.

In operation 809, the sharing relay device 20 transmits data informing the start of sharing to the health care device 10.

In operation 810, the health care device 10 transmits information about a web page to be shared to the sharing relay device 20.

In operation 811, the health information terminal 30 monitors the sharing relay device 20.

In operation 812, the sharing relay device 20 transforms the information about the to-be-shared web page received from the health care device 10 into an image and transmits the image to the health information terminal 30, in response to the monitoring of the health information terminal 30.

In operation 813, the health information terminal 30 monitors the sharing relay device 20.

In operation 814, the sharing relay device 20 transmits a signal which indicates that no data has been received from the health care device 10, to the health information terminal 30.

In operation 815, the health care device 10 transmits position information about a point or a portion on a to-be-shared image to the sharing relay device 20.

In operation 816, the health information terminal 30 monitors the sharing relay device 20.

In operation 817, the sharing relay device 20 transmits the position information received from the health care device 10 to the health information terminal 30 in response to the monitoring of the health information terminal 30.

In operation 818, the health information terminal 30 monitors the sharing relay device 20.

Accordingly, in an embodiment of a health information sharing system, image sharing and point or portion position sharing between the health care device 10, the sharing relay device 20, and the health information terminal 30 may be provided in real time. In another embodiment, the sharing method may be different.

According to the above-described method, images may be shared in real time without separately installing a web application for sharing a web page in the web environment. In addition, in tele-medicine, although a patient and a medical professional are remotely located from each other, the patient may accurately share points or portions indicated by the medical professional, thereby increasing the efficiency of consultation.

As further described above, real-time image sharing between a health care device and a health information terminal may be substantially ensured, and the load on the health care device which provides the health information of a user may be substantially reduced, thereby improving function. Without having to install a special web application, which may be used by a general-use computer to provide image sharing, in the health information terminal, real-time sharing of an image which represents the health information of the user is ensured, and a position pointed out by a health care service provider may also be shared in real time.

In addition, other aspects may also be implemented using at least one of a computer readable code, or instructions, which are in or on a medium, e.g., a computer readable medium, to control at least one processing element to implement at least one of the above described examples. The medium may correspond to any medium or media which can store and/or transmit computer readable code. The computer readable code may be recorded and/or transferred on a medium in a variety of ways, and examples of the medium include recording media, including magnetic storage media (e.g., read only memory ("ROM"), floppy disks, hard disks, or the like) and optical recording media (e.g., a compact disk "CD"-ROM, or a digital versatile disk, "DVD"), and transmission media such as Internet transmission media. Thus, the medium may be a defined and measurable structure including or carrying a signal or information, such as a device carrying a bitstream. The media may also be a distributed network, and the computer readable code may be stored and/or transferred and executed in a distributed fashion. Furthermore, the processing element may include a processor or a computer processor, and processing elements may be distributed and/or included in a single device.

It should be understood that the exemplary examples described herein should be considered in a descriptive sense only and not for purposes of limitation. Descriptions of features, advantages or aspects within each example should be considered as available for other features, advantages or aspects in other examples.

What is claimed is:

1. A method of displaying health information of a user, the method comprising:
    monitoring whether a sharing request for a health information of a user is made by an external device, wherein the external device provides a web page representing the health information of the user in the form of an image;
    downloading a captured image of the web page from the external device when the sharing request for the health information of the user is made; and
    displaying the downloaded captured image.

2. The method of claim 1, further comprising increasing a number of times the monitoring is performed when the sharing request for the health information of the user is made.

3. The method of claim 1, further comprising changing the number of times the monitoring is performed based on a health care schedule of the user.

4. The method of claim 1, wherein:
    the monitoring comprises monitoring whether a new image corresponding to the health information of the user is provided by the external device;
    the downloading of the captured image comprises downloading the new image from the external device when it is determined by the monitoring that the new image is provided; and
    the displaying of the downloaded captured image comprises displaying the new image.

5. The method of claim 1, wherein:
    the downloading of the captured image comprises downloading position information about at least a portion of the displayed image; and
    the displaying of the downloaded captured image comprises overlaying a mark on the at least a portion of the displayed image corresponding to the downloaded position information.

6. The method of claim 5, further comprising transforming the downloaded position information so that the downloaded position information conforms to a resolution of the displayed image,
    wherein the displaying of the downloaded captured image comprises overlaying a mark on the at least a portion of the displayed image corresponding to a result of the transformation.

7. The method of claim 1, further comprising decrypting the downloaded captured image, wherein the displaying comprises displaying the decrypted captured image.

8. The method of claim 1, further comprising:
    receiving an input signal corresponding to an input of the user; and
    transmitting the received input signal to the external device,
    wherein the input signal comprises at least one selected from the group consisting of information about a health of the user, information about inquiries of the user, a health care schedule of the user, and position information about at least a portion of the displayed image desired to be distinctively displayed on the displayed image.

9. A method of providing health information of a user in the form of an image, the method comprising:
    receiving a sharing request for sharing a health information of a user and a web page representing the health information of the user;
    transforming the web page into the form of an image;
    storing the image; and
    transmitting the stored image to a terminal of the user in response to a download request of the terminal of the user.

10. The method of claim 9, wherein the transforming comprises capturing a portion of the web page and transforming the captured portion into an image.

11. The method of claim 9, further comprising receiving position information about at least a portion of the captured image,
    wherein:
    the storing comprises storing the received position information; and
    the transmitting comprises transmitting the stored position information to the user's terminal in response to a request of the terminal of the user.

12. The method of claim 11, further comprising normalizing the received position information into standard position information, wherein the storing comprises storing the standard position information.

13. The method of claim 9, wherein:
the storing comprises storing the received sharing request; and
the transmitting comprises transmitting data indicating existence of the sharing request to the terminal of the user in response to a request of the terminal of the user.

14. The method of claim 9, further comprising encrypting the image, wherein:
the storing comprises storing the encrypted image; and
the transmitting comprises transmitting the encrypted image to the terminal of the user in response to a request of the terminal of the user.

15. The method of claim 9, further comprising checking an Internet protocol address of the terminal of the user,
wherein when the Internet protocol address is identical to a previously-stored Internet protocol address of the user, the transmitting further comprises transmitting the image to the terminal of the user in response to the request of the terminal of the user.

16. A non-transitory computer-readable recording medium having recorded thereon a computer program for executing a method of displaying health information of a user, the method comprising:
monitoring whether a sharing request for a health information of a user is made by an external device, wherein the external device provides a web page representing the health information of the user in the form of an image;
downloading a captured image of the web page from the external device when the sharing request for the health information of the user is made; and
displaying the downloaded captured image.

17. An apparatus for displaying health information of a user, the apparatus comprising:
a monitoring unit, which monitors if a sharing request for a health information of a user is made by an external device, which provides a web page representing the health information of the user in the form of an image;
a communications interface, which downloads a captured image of the web page from the external device, if the monitoring unit determines that the sharing request for the health information of the user is made; and
a display unit, which displays the downloaded captured image.

18. The apparatus of claim 17, further comprising a transformation unit, which transforms a resolution of the downloaded captured image into a resolution of the display unit and transforms position information about a point or a portion on the image downloaded from the external device,
wherein the position information conforms to the resolution of the display unit, and
wherein the display unit displays the image, which has the resolution of the display unit and overlays a mark on a point or a portion corresponding to the image, which has the resolution of the display unit.

19. An apparatus for providing health information of a user in the form of an image, the apparatus comprising:
a communications interface, which receive a sharing request for sharing a health information of a user and a web page representing the health information of the user;
a transformation unit, which transforms the web page into an image; and
a database, which stores the image;
wherein the communications interface, which transmits the stored image to a terminal of the user in response to a download request by the user's terminal.

20. A system for sharing a web page which represents health information of a user, the system comprising:
a health care device, which transmits a sharing request for a web page representing a health information of a user to a sharing relay device;
wherein the sharing relay device transforms a to-be-shared portion of the web page received from the health care device into an image, stores the image, and transmits the stored image to a terminal of the user in response to a download request of the user's terminal; and
a health information terminal, which monitors the sharing relay device to determine if a sharing request for the health information of a user is made by the health care device, wherein if the health information terminal determines that the sharing request for the health information of the user is made, downloading the stored image from the sharing relay device and displaying the downloaded image.

* * * * *